(12) United States Patent
Najarian et al.

(10) Patent No.: US 10,786,208 B2
(45) Date of Patent: Sep. 29, 2020

(54) SYSTEMS AND METHODS FOR PREDICTING AND DETECTING A CARDIAC EVENT

(71) Applicants: TOYOTA MOTOR ENGINEERING & MANUFACTURING NORTH AMERICA, INC., Plano, TX (US); THE REGENTS OF THE UNIVERSITY OF MICHIGAN, Ann Arbor, MI (US)

(72) Inventors: Kayvan Najarian, Ann Arbor, MI (US); Hendrikus Derksen, Ann Arbor, MI (US); Zhi Li, Ann Arbor, MI (US); Jonathan Gryak, Ann Arbor, MI (US); Pujitha Gunaratne, Ann Arbor, MI (US)

(73) Assignees: TOYOTA MOTOR ENGINEERING & MANUFACTURING NORTH AMERICA, INC., Plano, TX (US); THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 16/577,380

(22) Filed: Sep. 20, 2019

(65) Prior Publication Data

US 2020/0022658 A1 Jan. 23, 2020

Related U.S. Application Data

(63) Continuation of application No. 16/040,473, filed on Jul. 19, 2018, now Pat. No. 10,463,314.

(51) Int. Cl.
G08B 23/00 (2006.01)
A61B 5/00 (2006.01)
(Continued)

(52) U.S. Cl.
CPC .......... A61B 5/7275 (2013.01); A61B 5/0456 (2013.01); A61B 5/7282 (2013.01);
(Continued)

(58) Field of Classification Search
CPC ... A61B 5/7275; A61B 5/0456; A61B 5/7282; A61B 5/02405; A61B 5/046; A61B 5/0468; A61B 5/0472; A61B 5/18
(Continued)

(56) References Cited

U.S. PATENT DOCUMENTS 7,945,313 B2 5/2011 Fuwamoto
9,289,150 B1 * 3/2016 Gupta .................. A61B 5/7235
(Continued)

Primary Examiner — Naomi J Small
(74) Attorney, Agent, or Firm — Sheppard, Mullin, Richter & Hampton LLP; Hector A. Agdeppa; Daniel N. Yannuzzi

(57) ABSTRACT

Systems and methods for predicting and/or detecting cardiac events based on real-time biomedical signals are discussed herein. In various embodiments, a machine learning algorithm may be utilized to predict and/or detect one or more medical conditions based on obtained biomedical signals. For example, the systems and methods described herein may utilize ECG signals to predict and detect cardiac events. In various embodiments, patterns identified within a signal may be assigned letters (i.e., encoded as distributions of letters). Based on the known morphology of a signal, states within the signal may be identified based on the distribution of letters in the signal. When applied in the in-vehicle environment, drivers or passengers within the vehicle may be alerted when an individual within the vehicle is, or is about to, experience a cardiac event.

19 Claims, 10 Drawing Sheets

(51) Int. Cl.
*A61B 5/0456* (2006.01)
*A61B 5/0472* (2006.01)
*A61B 5/18* (2006.01)
*A61B 5/024* (2006.01)
*A61B 5/0468* (2006.01)
*A61B 5/046* (2006.01)

(52) U.S. Cl.
CPC .......... *A61B 5/02405* (2013.01); *A61B 5/046* (2013.01); *A61B 5/0468* (2013.01); *A61B 5/0472* (2013.01); *A61B 5/18* (2013.01)

(58) Field of Classification Search
USPC ...................................................... 340/573.1
See application file for complete search history.

(56) References Cited

U.S. PATENT DOCUMENTS

| | | | |
|---|---|---|---|
| 9,408,543 B1* | 8/2016 | Gupta | ............... A61B 5/04012 |
| 9,420,958 B2 | 8/2016 | Fung | |
| 2002/0099424 A1* | 7/2002 | Ferek-Petric | ...... A61N 1/37258 |
| | | | 607/60 |
| 2008/0001735 A1* | 1/2008 | Tran | ....................... G06F 19/00 |
| | | | 340/539.22 |
| 2013/0231947 A1* | 9/2013 | Shusterman | ....... A61B 5/02055 |
| | | | 705/2 |
| 2015/0018702 A1* | 1/2015 | Galloway | .............. A61B 5/044 |
| | | | 600/523 |
| 2015/0342540 A1 | 12/2015 | An | |
| 2016/0135706 A1 | 5/2016 | Sullivan | |
| 2016/0256064 A1 | 9/2016 | Estes, Jr. | |
| 2017/0124642 A1* | 5/2017 | Barnett | ............. G06Q 30/0269 |
| 2017/0236065 A1* | 8/2017 | Kirschnick | ............ G06N 7/005 |
| | | | 702/181 |
| 2018/0353139 A1* | 12/2018 | Speier | .................... A61B 5/055 |
| 2020/0000344 A1 | 1/2020 | Oel | |

* cited by examiner

SYSTEMS AND METHODS FOR PREDICTING AND DETECTING A CARDIAC EVENT

CROSS REFERENCE TO RELATED APPLICATIONS

This application is a continuation of U.S. patent application Ser. No. 16/040,473, filed Jul. 19, 2018, entitled "SYSTEMS AND METHODS FOR PREDICTING AND DETECTING A CARDIAC EVENT," the entire contents of which is incorporated herein by reference.

TECHNICAL FIELD

The disclosed technology relates generally to systems and methods for predicting and detecting cardiac events, and more particularly, some embodiments relate to systems and methods for predicting and detecting cardiac events in non-clinical noisy environments such as, in-vehicle environments, based on real-time biomedical signals received for drivers and/or passengers within the vehicle.

DESCRIPTION OF THE RELATED ART

Conventional systems for detecting or predicting cardiac events are typically limited to specific types of cardiac events (or other medical conditions) and are difficult to modify to identify other types of events. Conventional systems are also often over-reliant on identifying particular peaks in a biomedical signal (e.g., an ECG signal) and fail to consider motion of the subject or other factors such as the environment noise, in detecting or predicting a potential medical condition. Additionally, conventional systems are typically designed to either detect or predict a medical condition (such as a cardiac event), but are rarely able to do both. There is a need for a means to both reliably detect and predict multiple types of medical conditions simultaneously.

BRIEF SUMMARY OF EMBODIMENTS

The systems and methods described herein may be used to detect and/or predict cardiac events based on real-time biomedical signals obtained from an individual. In various embodiments, a machine learning algorithm may be used to detect and/or predict the cardiac events. Training data obtained may comprise of a plurality of biomedical signals ("training signals"). Pre-event signals may be extracted from the training data that span a predetermined time interval before occurrence of a particular cardiac event. The training data may be analyzed to compute a sequence of conditional probability vectors. The pre-event signals may be applied to a Markov chain algorithm to train the machine learning algorithm based on the sequence of probability vectors obtained by analyzing the training signals, resulting in trained Markov transition matrices. The trained Markov transition matrices may be applied to a signal obtained from an individual in real-time to automatically predict an upcoming cardiac event for that individual. In various embodiments, the training signals and signals obtained in real-time may be pre-processed to remove noisy signals and/or enhance the signal ultimately utilized.

Unlike conventional systems which rely on recognized peaks associated with a signal (e.g., R-peak in an ECG signal), the systems and methods described herein do not rely on peak detection to analyze a signal. The systems and methods described herein instead identify certain forms in a signal and the frequency with which the form appears to identify patterns. The identified patterns are assigned letters (i.e., encoded into distributions of letters, such as distribution "Q"). In various embodiments, identified patterns may be encoded as letters, numbers, and/or other identifiers. Based on the known morphology of a signal, the Markov model is able to identify states in the signal based on the distribution of letters in the signal. For example, the Markov model may consider domain knowledge associated with one or more medical conditions and biomedical signals to identify states associated with a particular pattern. For example, based on the temporal relationship between multiple patterns in a ECG signal, the Markov model may be configured to determine that a first pattern assigned the arbitrary letter "x" is an R-peak and that a second pattern assigned the arbitrary letter "y" is a peaked P-wave. As such, the systems and methods described herein do not rely on peak detection, but instead are able to analyze a signal based on the patterns identified therein.

In some embodiments, the systems and methods described herein may be configured to generate an alert and cause the alert to be communicated when a cardiac event has been predicted or detected. In some embodiments, the systems and methods described herein may be configured to predict and/or detect cardiac events in an in-vehicle environment based on real-time biomedical signals received for drivers and/or passengers within the vehicle. In the in-vehicle environment, the systems and methods described herein may be configured to generate an alert and cause the alert to be provided to a driver, a passenger, and/or the authorities. In some embodiments, the system may automatically slow the vehicle and/or actuate other safety maneuvers in response to a predicted or detected cardiac event.

The system may include one or more hardware processors configured by machine-readable instructions. Executing the machine-readable instructions may cause the one or more processors to predict and/or detect cardiac events based on real-time biomedical signals obtained from an individual. The one or more physical processors may represent processing functionality of multiple components of the system operating in coordination. Therefore, the various processing functionality described in relation to the one or more processors may be performed by a single component or by multiple components of the system.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

Embodiments of the technology disclosed herein are directed toward systems and methods for predicting and/or detecting medical conditions of an individual based on one or more obtained biomedical signals. In various embodiments, the systems and methods disclosed herein may be configured to predict and/or detect medical conditions (e.g., a cardiac event) in an in-vehicle environment based on real-time biomedical signals received for drivers and/or passengers within the vehicle.

In various embodiments, the systems and methods disclosed herein may be configured to predict and/or detect cardiac events, such as Atrial Fibrillation (or AFib) events, in real-time based on biomedical signals received for an individual. Atrial Fibrillation is a common cardiac arrhythmia with symptoms ranging from nonexistent to severe. Prediction of abnormal heart rates or AFib events may help prevent life-threatening conditions like stroke or heart failure. Typically, monitoring a patient with AFib requires monitoring an electrocardiogram (ECG) signal of the patient. An ECG signal comprises numerous components, including a P-wave (representing depolarization of the atria), the QRS complex and R-peak (representing the rapid depolarization of the right and left ventricles), and the T-wave (representing the repolarization of the ventricles).

Most existing monitoring systems require long-term hospitalization. The systems and methods described herein are directed to systems and methods that may be used to predict and/or detect cardiac events, such as episodes associated with AFib, ventricular fibrillation, ventricular tachycardia, supraventricular tachycardia, bradycardia, myocardial infarction, and/or one or more other types of cardiac events. The systems and methods described herein may be used to predict and/or detect cardiac events either inside or outside of a hospital environment. For example, the systems and methods described herein may be implemented in an environment remote from a hospital where clinicians able to diagnose a cardiac event are not available, in the home, in the hospital to assist clinicians, in an in-vehicle environment where sudden cardiac events can be dangerous to the drivers, the passengers, and other individuals on the road, and/or one or more other environments inside or outside a hospital environment.

Figure 1:
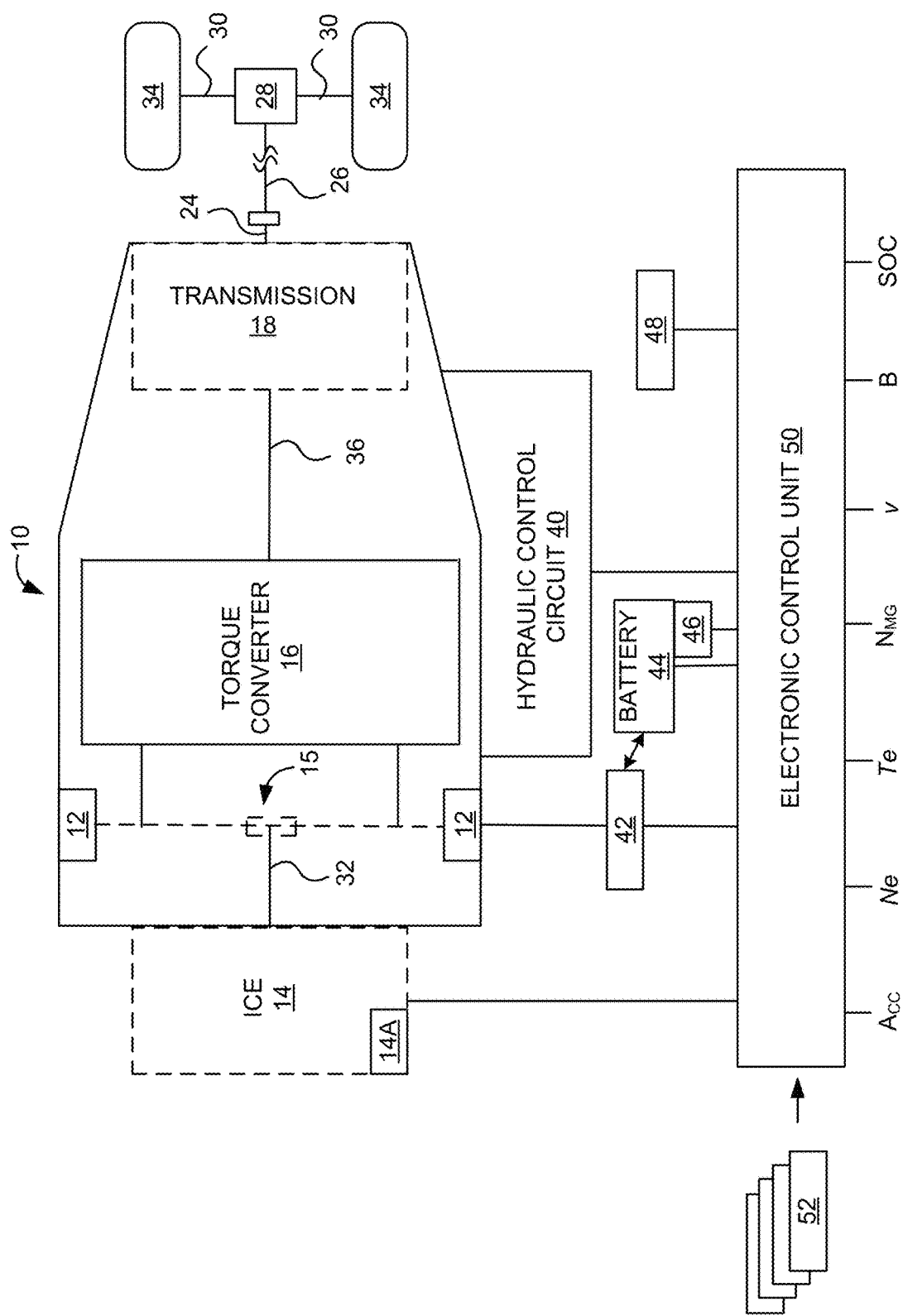
FIG. 1 illustrates an example of a vehicle with which systems and methods for predicting and/or detecting cardiac events may be implemented, in accordance with one embodiment of the systems and methods described herein.

In some embodiments, the technology disclosed herein may be implemented in any of a number of different vehicle types including, for example, automobiles, trucks, buses, boats and ships, and other vehicles. An example vehicle, such as a hybrid electric vehicle (HEV), in which a camera vehicle activation system may be implemented is illustrated in FIG. 1. FIG. 1 illustrates an example of a hybrid electric vehicle 10 that may include an internal combustion engine 14 and one or more electric motors 12 as sources of motive power. Driving force generated by the internal combustion engine 14 and motor 12 can be transmitted to one or more wheels 34 via a torque converter 16, a transmission 18, a differential gear device 28, and a pair of axles 30.

As an HEV, vehicle 10 may be driven/powered with either or both of engine 14 and the motor(s) 12 as the drive source for travel. For example, a first travel mode may be an engine-only travel mode that only uses ICE 14 as the drive source for travel. A second travel mode may be an EV travel mode that only uses the motor(s) 12 as the drive source for travel. A third travel mode may be an HEV travel mode that uses engine 14 and the motor(s) 12 as drive sources for travel. In the engine-only and HEV travel modes, vehicle 10 relies on the motive force generated at least by ICE 14, and a clutch 15 may be included to engage engine 14. In the EV travel mode, vehicle 10 is powered by the motive force generated by motor 12 while engine 14 may be stopped and clutch 15 disengaged.

Engine 14 can be an internal combustion engine such as a gasoline, diesel or similarly powered engine in which fuel is injected into and combusted in a combustion chamber. An output control circuit 14A may be provided to control drive (output torque) of engine 14. Output control circuit 14A may include a throttle actuator to control an electronic throttle valve that controls fuel injection, an ignition device that controls ignition timing, and the like. Output control circuit 14A may execute output control of engine 14 according to a command control signal(s) supplied from an electronic control unit 50, described below. Such output control can include, for example, throttle control, fuel injection control, and ignition timing control.

Motor 12 can also be used to provide motive power in vehicle 10, and is powered electrically via a power storage device 44. Motor 12 can be powered by power storage device 44 to generate a motive force to move the vehicle and adjust vehicle speed. Motor 12 can also function as a generator to generate electrical power such as, for example, when coasting or braking. Power storage device 44 may also be used to power other electrical or electronic systems in the vehicle. Motor 12 may be connected to power storage device 44 via an inverter 42. Power storage device 44 can include, for example, one or more batteries, capacitive storage units, or other storage reservoirs suitable for storing electrical energy that can be used to power one or more motors 12. When power storage device 44 is implemented using one or more batteries, the batteries can include, for example, nickel metal hydride batteries, lithium ion batteries, lead acid batteries, nickel cadmium batteries, lithium ion polymer batteries, and other types of batteries.

An electronic control unit 50 (described below) may be included and may control the electric drive components of the vehicle as well as other vehicle components. For example, electronic control unit 50 may control inverter 42, adjust driving current supplied to motors and adjust the current received from motors 12 during regenerative coasting and breaking. As a more particular example, output torque of the motor 12 can be increased or decreased by electronic control unit 50 through the inverter 42.

A torque converter 16 can be included to control the application of power from engine 14 and motors 12 to transmission 18. Clutch 15 can be included to engage and disengage engine 14 from the drivetrain of the vehicle. In the illustrated example, a crankshaft 32, which is an output member of engine 14, may be selectively coupled to the motors 12 and torque converter 16 via clutch 15.

As alluded to above, vehicle 10 may include an electronic control unit 50. Electronic control unit 50 may include circuitry to control various aspects of the vehicle operation. Electronic control unit 50 may include, for example, a microcomputer that includes one or more processing units (e.g., microprocessors), memory storage (e.g., RAM, ROM, etc.), and I/O devices. The processing units of electronic control unit 50, execute instructions stored in memory to control one or more electrical systems or subsystems in the vehicle. Electronic control unit 50 can include a plurality of electronic control units such as, for example, an electronic engine control module, a powertrain control module, a transmission control module, a suspension control module, a body control module, and so on. As a further example, electronic control units can be included to control systems and functions such as doors and door locking, lighting, human-machine interfaces, cruise control, telematics, braking systems (e.g., ABS or ESC), battery management systems, and so on. These various control units can be implemented using two or more separate electronic control units, or using a single electronic control unit.

Figure 9:
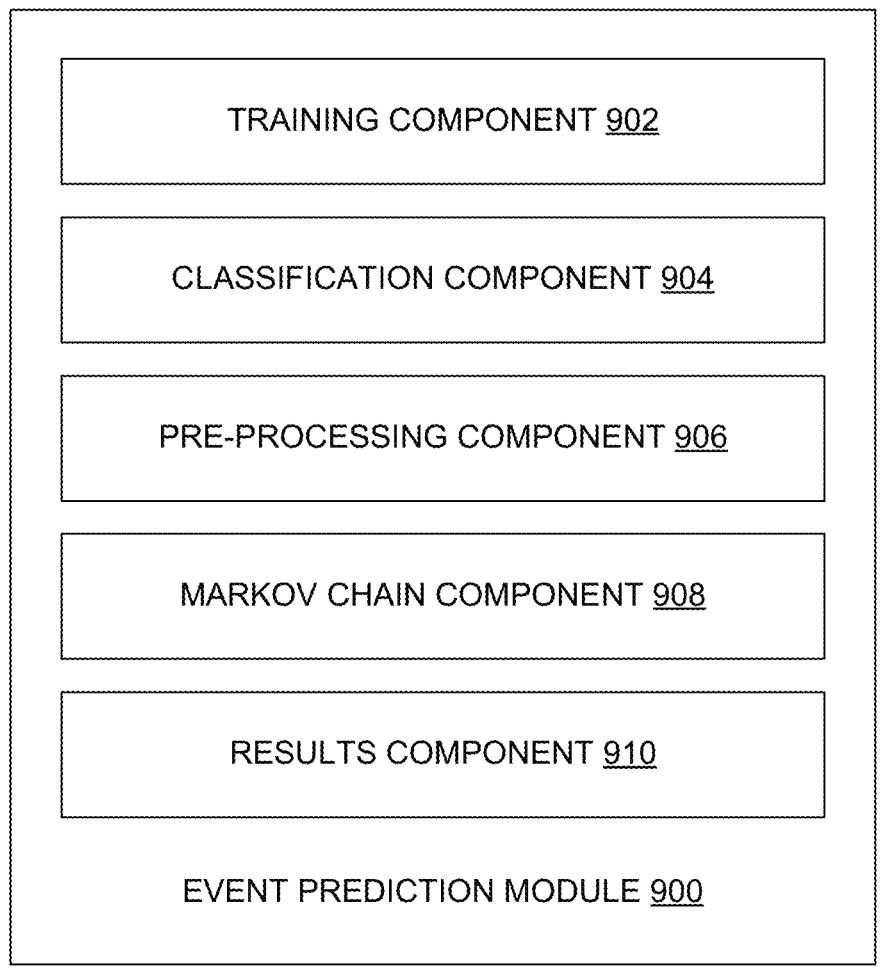
FIG. 9 illustrates an example of a block diagram of an event prediction module configured to predict and/or detect medical conditions based on one or more obtained biomedical signals, in accordance with various embodiments.

In various embodiments, electronic control unit 50 may include or be communicatively coupled to an event prediction module, such as event prediction module 900 depicted in FIG. 9. In some embodiments, the event prediction module may interface with electronic control unit 50 and/or one or more other in-vehicle components. In some embodiments, electronic control unit 50 may be configured control one or more in-vehicle components based on a medical condition predicted or detected by event prediction module. For example, electronic control unit 50 may be configured to cause an alert to be communicated in response to the prediction or detection of a cardiac event by event prediction module. In some embodiments, electronic control unit 50 may be configured to generate an alert and cause the alert to be provided to a driver, a passenger, and/or the authorities in response to the prediction or detection of a cardiac event by event prediction module. For example, electronic control unit 50 may be configured to automatically cause an alert to be displayed via an in-vehicle display of the vehicle. In some embodiments, an alert may be provided to other individuals on or near the roadway via the activation of emergency lights on the vehicle. In some embodiments, electronic control unit 50 may be configured to automatically slow the vehicle in response to the prediction or detection of a cardiac event by event prediction module.

In the example illustrated in FIG. 1, electronic control unit 50 receives information from a plurality of sensors included in vehicle 10. For example, electronic control unit 50 may receive signals that indicate vehicle operating conditions or characteristics, signals that can be used to derive vehicle operating conditions or characteristics, signals that indicate a medical condition of a driver and/or passenger(s) of vehicle 10 (i.e., one or more biomedical signals), and/or one or more other signals. These may include, but are not limited to accelerator operation amount, $A_{CC}$, a revolution speed, $N_E$, of ICE 14 (engine RPM), a rotational speed, $N_{MS}$, of the motor 12 (motor rotational speed), and vehicle speed, $N_V$. These may also include torque converter 16 output, $N_T$ (e.g., output amps indicative of motor output), brake operation amount, B, battery SOC (i.e., the charged amount for battery 44 detected by an SOC sensor). Accordingly, vehicle 10 can include a plurality of sensors 52 that can be used to detect various conditions internal or external to the vehicle and provide sensed conditions to engine control unit 50 (which, again, may be implemented as one or a plurality of individual control circuits). In one embodiment, sensors 52 may be included to detect one or more conditions directly or indirectly such as, for example, fuel efficiency, $E_F$, motor efficiency, $E_{MG}$, hybrid (ICE 14+motor 12) efficiency, etc.

In some embodiments, one or more of the sensors 52 may include their own processing capability to compute the results for additional information that can be provided to electronic control unit 50. In other embodiments, one or more sensors may be data-gathering-only sensors that provide only raw data to electronic control unit 50. In further embodiments, hybrid sensors may be included that provide a combination of raw data and processed data to electronic control unit 50. Sensor 52 may provide an analog output or a digital output.

Additional sensors 52 may be included to detect vehicle conditions as well as to detect external conditions. Sensors that might be used to detect external conditions can include, for example, sonar, radar, lidar or other vehicle proximity sensors, and cameras or other image sensors. Cameras, or image capture devices can be used to detect, for example, road conditions in the region in front and all around the vehicle and so on. Still other sensors may include those that can detect road grade. While some sensors can be used to actively detect passive environmental objects, other sensors can be included and used to detect active objects such as those objects used to implement smart roadways that may actively transmit and/or receive data or other information.

In various implementations, one or more sensors configured to monitor a biomedical signal of a driver and/or passenger(s) of vehicle 10 may be incorporated into vehicle 10. For example, a sensor configured to monitor a biomedical signal (e.g., an ECG signal) may be incorporated into a steering wheel, a seat, and/or other components in contact with or within a proximity of the driver and/or passenger(s). Biomedical signals obtained via one or more sensors incorporated into vehicle 10 may be provided to the event prediction module.

Event prediction module may be configured to predict and/or detect one or more medical conditions based on obtained biomedical signals. In various embodiments, event prediction module may be configured to utilize a machine learning algorithm to predict and/or detect one or more medical conditions based on obtained biomedical signals. The event prediction module may be configured to obtain training data comprising a plurality of biomedical signals ("training signals"). The event prediction module may be configured to extract pre-event signals from the training data that span a predetermined time interval before a particular cardiac event. The event prediction module may be configured to analyze the training data to compute conditional probability vectors. The event prediction module may be configured to apply the pre-event signals to a Markov chain algorithm to train the machine learning algorithm based on the sequence of probability vectors obtained by analyzing the training signals, resulting in trained Markov transition matrices. The event prediction module may be configured to apply the trained Markov transition matrices to a signal obtained from an individual in real-time to automatically predict an upcoming cardiac event for the individual. In some embodiments, the training signals and signals obtained in real-time may be pre-processed to remove noisy signals and/or enhance the signal ultimately utilized.

In some embodiments, the event prediction module may be configured to predict and/or detect one or more medical conditions based on a single biomedical signal or multiple biomedical signals simultaneously. For example, the event prediction module may be configured to predict and/or detect one or more medical conditions based on ECG signals and/or photoplethysmogram (PPG) signals simultaneously. In various embodiments, the event prediction module described herein may be the same or similar to event prediction module 900 depicted in FIG. 9.

In various exemplary embodiments, the biomedical signals may comprise electrocardiogram (ECG) signals, and the ECG signals may be utilized by event prediction module to predict and/or detect one or more cardiac events, such as an episode of Atrial Fibrillation (AFib). This is a non-limiting example, and the features of the systems and methods described herein may utilize one or more other types of biomedical signals to detect other medical conditions.

In an exemplary embodiment, event prediction module may be configured to train a Markov model and associated classifications by encoding a biomedical signal (e.g., an ECG signal) as word distributions. For example, a finite alphabet "$\Sigma$" may be used, in which "$\Sigma^*$" is the set of all words in the alphabet "$\Sigma$", including the empty word "$\varepsilon$". The length of a word "$(\Omega \in \Sigma^*)$" is denoted by "$l(\omega)$". If "$\Sigma = \{\alpha_1, \alpha_2 \ldots \alpha_d\}$" is an alphabet, then a word distribution of length "n" is a "d×n" matrix "Q". For example, a random word "$\omega = \omega_1 \omega_2 \ldots \omega_n$" of length "n" has probability distribution "Q" if the letters "$\omega_1, \omega_2, \ldots, \omega_n$" are independent of each other, and "$Q_{i,j} = P(\omega_j = a_i)$" is the probability that the "j-th" letter of the word "$\omega$" is the letter "$a_1$". For a given word "$u$" of length "$n$", the probability "$P(\omega = u)$" that "$\omega$" is equal to "$u = a_{i_1} a_{i_2} \ldots a_{i_n}$" is equal to "$\Pi_{j=1}^{n} Q_{i_j,j}$".

In an exemplary embodiment, the Markov model utilized by event prediction module may comprise Markov Model "M". Markov Model "M" is a set "S" of states, an alphabet "$\Sigma$", together with a transition function "T:S$\Sigma \to$S" and a probability function "P: S×$\Sigma \to$[0,1]". If in state "s$\in$S", then with probability "P(s, a)", the model will transition to the state "T(s, a)" and produce the letter "a" as output. An initial state "$\iota \in S$" may be specified. For a word "w", "M(w)" may be the state of the automaton if beginning in the initial state and the output of the output is the word "w". Accordingly, "$M(\varepsilon) = \iota$" and $$M(w_1 w_2 \ldots w_k) = T(M(w_1 w_2 \ldots w_{k-1}), w_k).$$

The Markov Model can be thought of as a random word generator. The probability that Markov model "M" produces the output "w" after "n=l(w)" steps starting at the initial state will be denoted by "P(w|M)". The alphabet may be represented by "$\Sigma = \{a_1, a_2, \ldots, a_d\}$". The set of states may be represented by "$S = \{s_1 = \varepsilon, s_2, \ldots, s_m\}$". The functions "P" and "T" may be represented by "m×d" matrices "P" and "T" so that "$P_{ij} = P(s_i, a_j)$" for all "i" and "j", and "$T_{ij} = k$" if "$T(s_i, a_j) = s_k$" for all "i,j,k".

In various embodiments, the event prediction module may be configured to obtain training data comprising a plurality of biomedical signals ("training signals"). In some embodiments, the event prediction module may be configured to obtain training data from a database associated with a particular biomedical signal. In an exemplary embodiment in which the biomedical signal comprises an ECG signal, the training data may be obtained from the Physionet/CinC 2017 database, and/or one or more other databases that store ECG signals. In some embodiments, signals obtained from individuals in real-time may be stored and later used to train a machine learning algorithm to predict and/or detect one or more medical conditions. For example, signals obtained from individuals in real-time may be stored as training data in main memory (e.g., main memory 808) and/or one or more storage devices (e.g., storage devices 810).

Figure 2:
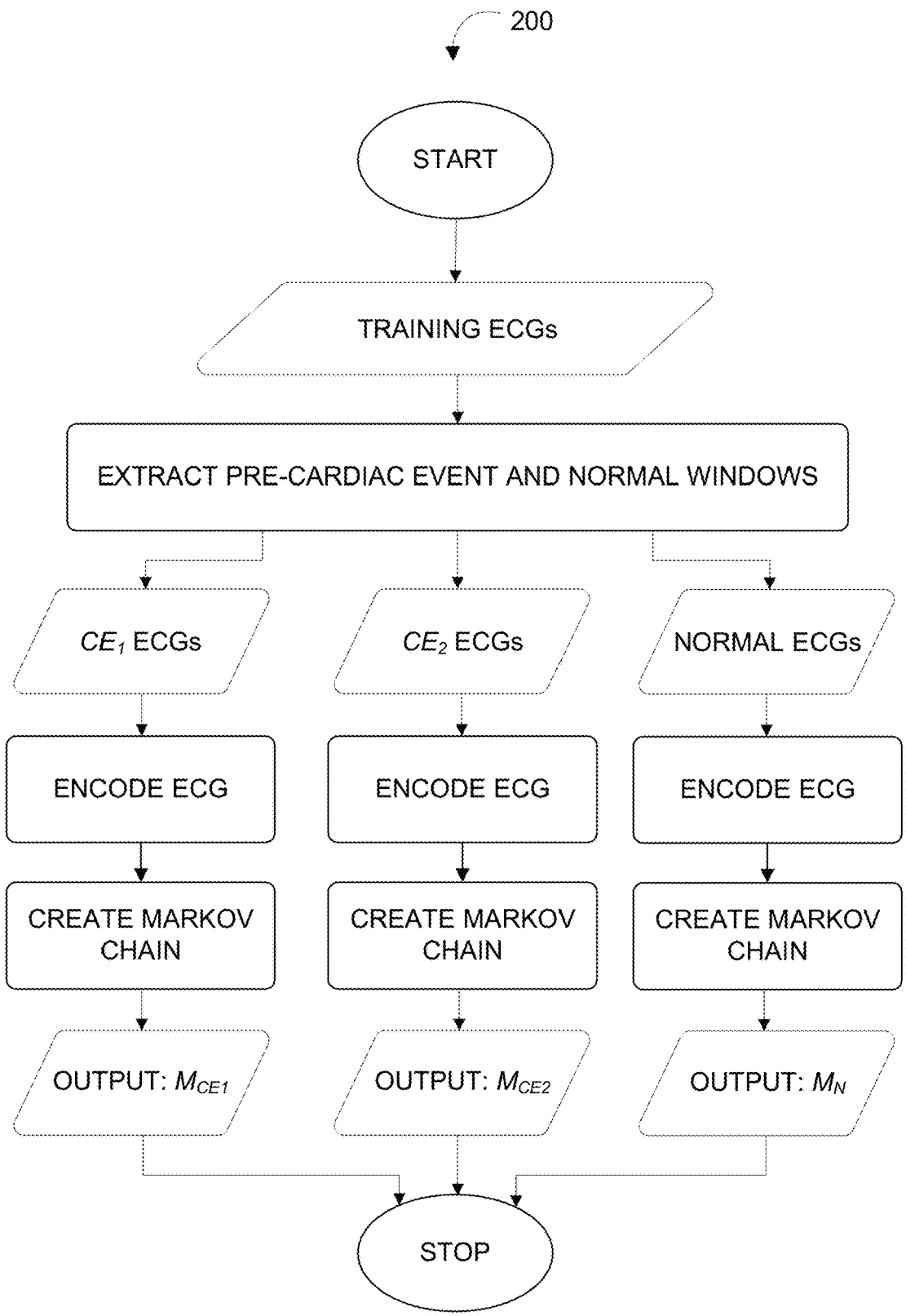
FIG. 2 contains an operational flow diagram illustrating an example workflow for training a model used to predict and/or detect a cardiac event, in accordance with various embodiments.

In various embodiments, the event prediction module may be configured to train a model used to predict and/or detect a cardiac event. Referring to FIG. 2, an operational flow diagram is depicted illustrating an example workflow 200 for training the model used to predict and/or detect one or more medical conditions, in accordance with various embodiments. In various implementations, the event prediction module may be configured to predict and/or detect several types of cardiac events, which may be denoted $CE_1$, $CE_2$, $\ldots$, $CE_r$. For example, $CE_1$ may comprise atrial fibrillation, $CE_2$ may comprise ventricular tachycardia, and $CE_3$, $\ldots$, $CE_r$ may comprise one or more other types of cardiac events. The event prediction module may be configured to obtain training data (e.g., training ECGs). The obtained training data may be used to train the model. For example, the training data may comprise one or more biomedical signals from healthy individuals and one or more biomedical signals from unhealthy individuals (e.g., ECGs related to $CE_1$, $CE_2$, $\ldots$, $CE_r$). In various embodiments, biomedical signals from multiple healthy individuals and multiple unhealthy individuals may be utilized as training data simultaneously. In an exemplary embodiment (as depicted in FIG. 2), the training data may comprise one or more training ECG signals. In various embodiments, the features described herein to train the model used to predict and/or detect one or more medical conditions may be performed by training component 902 of event prediction module 900 depicted in FIG. 9.

Referring back to FIG. 2, the event prediction module may be configured to extract windows that precede a future cardiac event (CE) and windows that do not contain or precede cardiac events. In an exemplary embodiment, the event prediction module may be configured to extract windows that are indicative of future AFib episodes (Pre-AFib ECGs) and windows that are normal (Normal ECGs). In some embodiments, the event prediction module may be configured to extract pre-event signals from the training data that span a predetermined time interval before a particular cardiac event. For example, an ECG signal more than a predetermined time interval (e.g., 2 minutes) prior to a cardiac event may not provide any indication of the oncoming cardiac event. As such, the ECG signal more than the predetermined time interval prior to the cardiac event may not be relevant training data. In various embodiments, the event prediction module may be configured to extract only the signals from the training data that span the predetermined time interval before a particular cardiac event and signals for a window that are normal that is of the same length as the predetermined time interval. Referring to FIG. 2, the event prediction module may be configured to predict and/or detect two cardiac events (i.e., where r=2). In the embodiment of FIG. 2, the event prediction module may be configured to extract from signals related to $CE_1$ a predetermined time interval prior to the cardiac event $CE_1$ (denoted $CE_1ECGs$), extract from signals related to $CE_2$ the predetermined time interval prior to the cardiac event $CE_2$ (denoted $CE_2ECGs$), and extract from healthy signals the predetermined time interval (denoted Normal ECGs). In various implementations, event prediction module may be configured to encode extracted signals (e.g., $CE_1ECGs$, $CE_2ECGs$, and Normal ECGs) into word distributions. Encoded signals related to future cardiac event (CE) (i.e., $CE_1$, $CE_2$, ..., $CE_r$) are utilized to create Markov models for the cardiac events. For example, event prediction module may be configured to utilize the encoded $CE_1ECGs$ to create a Markov model "$M_{CE1}$", and utilize the encoded $CE_2ECGs$ to create a Markov model "$M_{CE2}$". The event prediction module may be configured to utilize the encoded Normal ECGs to create a Markov model "$M_n$". In some embodiments, the encoded ECGs are utilized to create Markov models as described in example workflow 500 for creating a Markov chain algorithm depicted in FIG. 5.

Figure 3:
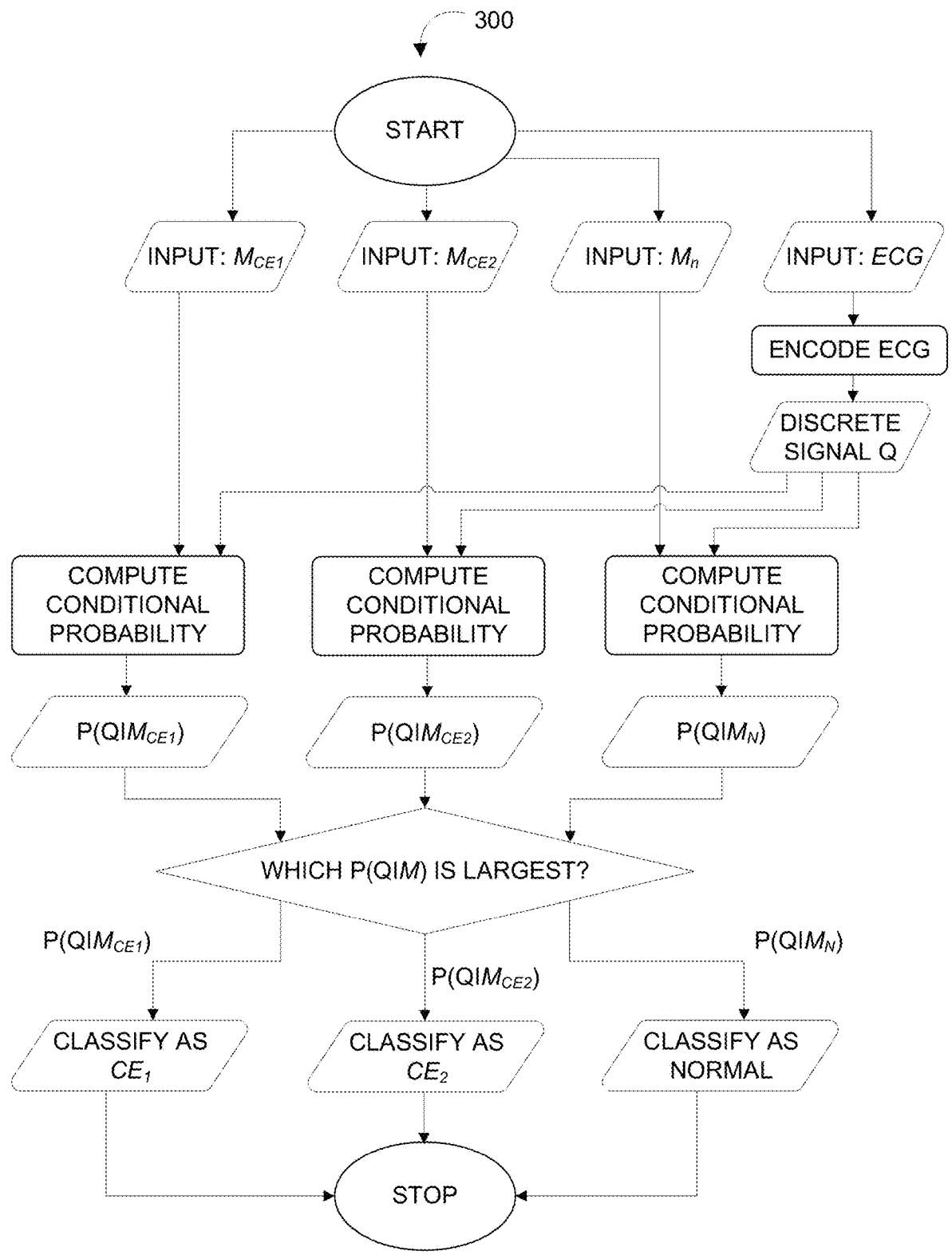
FIG. 3 contains an operational flow diagram illustrating an example workflow for classifying conditions based on one or more biomedical signals, in accordance with various embodiments.

In various embodiments, event prediction module may be configured to classify normal medical conditions (i.e., corresponding to a healthy individual) based on a Markov model created utilizing normal ECGs (e.g., "$M_n$") and classify non-normal medical conditions (i.e., corresponding to an unhealthy individual) based on the Markov models created utilizing ECG windows that precede a future cardiac event (CE) (e.g., "$M_{CE1}$" and "$M_{CE2}$"). For example, a non-normal medical condition may comprise a Pre-AFib state that is classified based on one or more obtained biomedical signals comprising at least an ECG signal. Referring to FIG. 3, an operational flow diagram is depicted illustrating an example workflow 300 for classifying conditions based on one or more biomedical signals, in accordance with various embodiments. The biomedical signal may be obtained as described herein and stored as test data in main memory (e.g., main memory 808) and/or one or more storage devices (e.g., storage devices 810). For example, the biomedical signal may comprise an ECG signal. The signal may be encoded into a word distribution "Q", as described further herein. In various embodiments, the event prediction module may be configured to analyze the training data to compute conditional probability vectors. For example, based on the Markov models "$M_{CE_1}$" and "$M_{CE_2}$" for the pre-cardiac event case and the Markov model "$M_n$" for the Normal case obtained during the training phase described above, event prediction module may be configured to compute conditional probabilities that the ECG signal represents a pre-cardiac event state (which may be denoted "$CE_1$, $CE_2$, ..., $CE_r$") or a "Normal" state. For example, event prediction module may be configured to compute:

$$P(Q|M_{CE_i}) = E(P(u|M_{CE_i})) = \Sigma P(w=u|M_{CE_i})P(u),$$

wherein "$P(Q|M_{CE_i})$" is the expected probability that the Markov model "$M_{CE_i}$" produced the random word "w" (with probability distribution "Q"). Similarly, event prediction module may be configured to compute the expected probability "$P(Q|M_n)$" that the Markov model "$M_n$" produced the random word "w" with distribution "Q". If "$P(Q|M_n)$" is greater than "$P(Q|M_{CE_i})$", the event prediction module is configured to classify the ECG as "Normal". If "$P(Q|M_{CE_i})$" is the largest among $$P(Q|M_n), P(Q|M_{CE_1}), P(Q|M_{CE_2}), \ldots P(Q|M_{CE_r})$$

the event prediction module is configured to classify the ECG as having $CE_i$. Thus, in the exemplary embodiment depicted in FIG. 3, wherein $CE_1$ comprises AFib and $CE_2$ comprises ventricular tachycardia, event prediction module may be configured to classify a biomedical signal input in workflow 300 as $CE_1$ if "$P(Q|M_{CE_1})$" is the largest among $P(Q|M_n)$, $P(Q|M_{CE_1})$, $P(Q|M_{CE_2})$, and classify the biomedical signal input in workflow 300 as $CE_2$ if "$P(Q|M_{CE_2})$" is the largest among $P(Q|M_n)$, $P(Q|M_{CE1})$, $P(Q|M_{CE2})$. In various embodiments, the features described herein to classify conditions based on one or more biomedical signals to further train the machine learning algorithm may be performed by classification component 904 of event prediction module 900 depicted in FIG. 9.

To calculate conditional probability "P(Q|M)", the Markov model may be represented by "M=(P, T)", where "P" is the "m×d" probability matrix, "T" is the "m×d" transition matrix, and "Q" is a word distribution. For "k=1, 2, ..., d", event prediction module creates a (sparse) matrix "$A^{(k)}$" of size "m×m" such that "$A_{i,k}^{(j)}=P_{i,j}$" when "$T_{i,j}=k$" and all other entries are 0. Suppose that "$u=u_1u_2 \ldots u_n$" is a random word with word distribution "Q". Let $$v_k = (v_{k,1} v_{k,2} \ldots v_{k,m}) \in \mathbb{R}^m$$

be the probability distribution over all m states of the Markov after reading the word $u_1 \ldots u_k$. This is expressed in the formula $$v_{k,j} = E(P(w_1 \ldots w_k = u_1 \ldots u_k M(w_1 \ldots w_k) = s_j)).$$

The initial state is $v_0=(1, 0, \ldots, 0)$, and for k>0 we have the recurrence $$v_k = v_{k-1}(Q_{1,k}A^{(1)} + Q_{2,k}A^{(2)} + \ldots + Q_{d,k}A^{(d)}).$$

As a result, $$P(Q|M) = E(P(u|M)) = \Sigma_j E(P(w=u|M(w)=s_j)) = \Sigma_j v_{k,j}$$

In the foregoing implementation, P(Q|M) may be extremely small, possibly leading to rounding errors. As a result, log P(Q|M) may instead be computed. In some implementations, $v_{k,j} = e^{\lambda_k} z_{k,j}$ where $\Sigma_j z_{k,j}=1$ and $\lambda_k z_{j,k}$ may be computed inductively, resulting in log $P(Q|M)=\lambda_n$.

In various embodiments, event prediction module may be configured to pre-process a biomedical signal that is used to predict and/or detect a medical condition (or train a model used to predict and/or detect a medical condition). For example, event prediction module may be configured to pre-process an ECG signal used predict and/or detect a cardiac event. In various embodiments, biomedical signals may be encoded into distributions of binary words. In some embodiments, biomedical signals may be encoded into distributions comprising larger alphabets. The word distributions for a signal may be based on patterns identified within the signal. Unlike conventional systems which rely on recognized peaks associated with a signal (e.g., R-peak in an ECG signal), the systems and methods described herein do not rely on peak detection to analyze a signal. The systems and methods described herein instead identify certain forms in a signal and the frequency with which the form appears to identify patterns. The identified patterns are assigned letters (i.e., encoded into distributions of words, such as distribution "Q"). In various embodiments, identified patterns may be encoded as letters, numbers, and/or other identifiers. Based on the known morphology of a signal, the Markov model is able to identify states in the signal based on the distribution of words in the signal. For example, the Markov model may consider domain knowledge associated with one or more medical conditions and biomedical signals to identify states associated with a particular pattern. For example, based on the temporal relationship between multiple patterns in a ECG signal, the Markov model may be configured to determine that a first pattern assigned the arbitrary letter "x" is an R-peak and that a second pattern assigned the arbitrary letter "y" is peaked P-wave. As such, the systems and methods described herein do not rely on peak detection, but instead are able to analyze a signal based on the patterns identified therein.

Figure 4A:
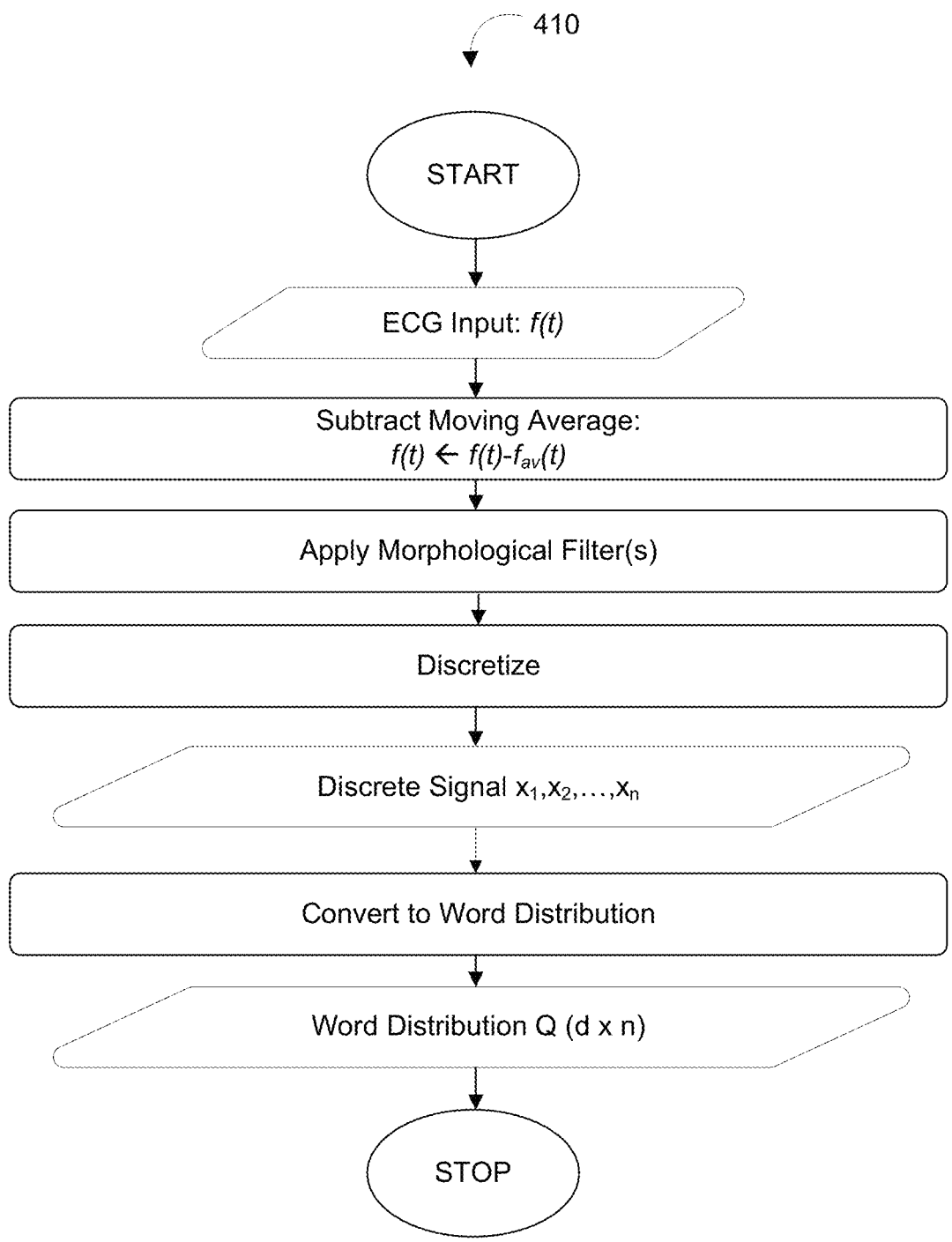
FIG. 4A contains an operational flow diagram illustrating an example workflow for pre-processing a biomedical signal, in accordance with various embodiments.
Figure 4B:
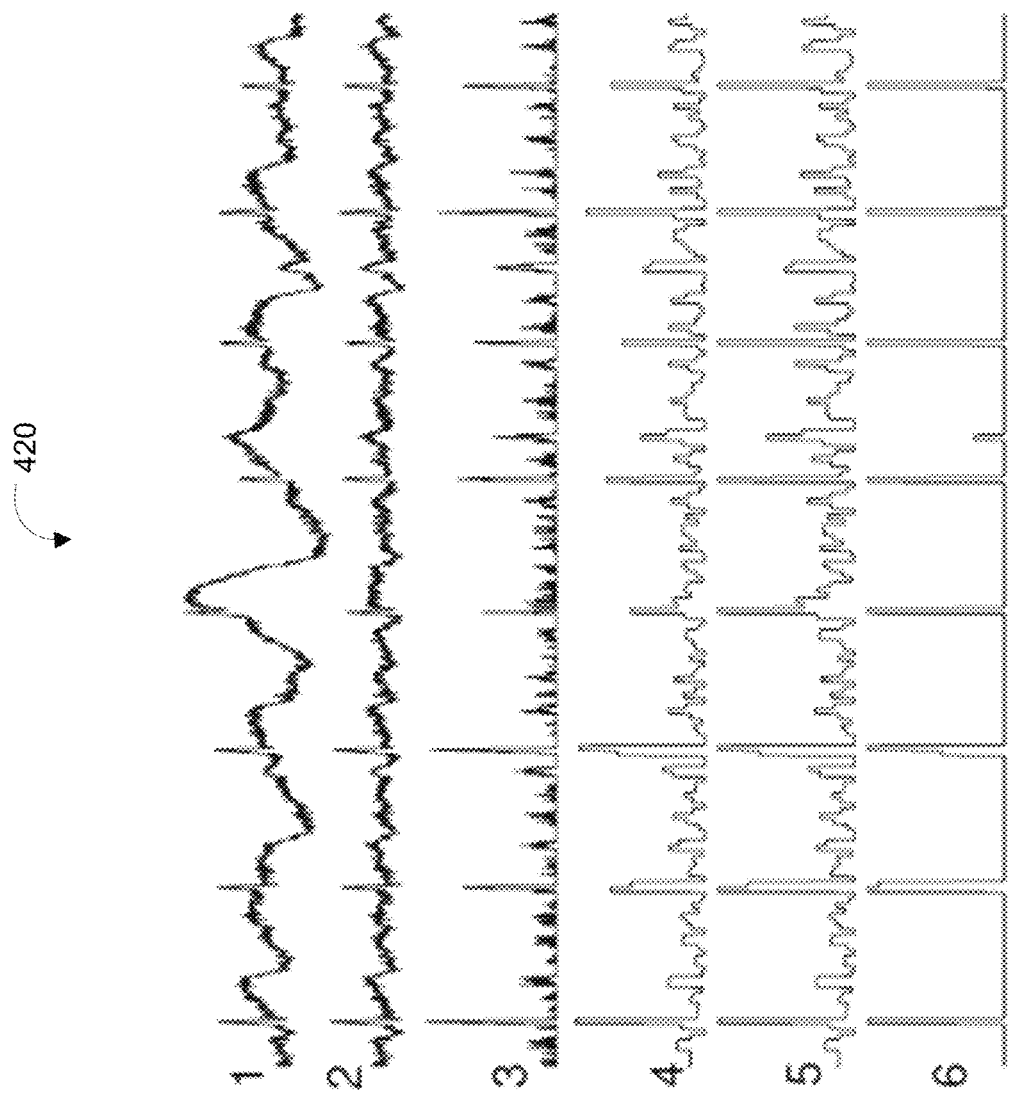
FIG. 4B illustrates an example of a biomedical signal at different stages of filtering and encoding, in accordance with various embodiments.

Referring to FIG. 4A, an operational flow diagram is depicted illustrating an example workflow 400 for pre-processing a biomedical signal, in accordance with various embodiments. In an exemplary embodiment, an ECG signal may be represented by "f(t)" where "t" is time in seconds, "0≤t≤$t_0$" and "$t_0$" is the length of the ECG recording. In some embodiments, the ECG signal—"f(t)" may be considered a continuous signal, but in some implementations it will be discrete with a large frequency (typically ≥200 Hz). In an exemplary embodiment in which the biomedical signal comprises an ECG signal, pre-processing may comprise baseline removal, applying one or more morphological filters (e.g., peak filtering, and/or one or more other morphological filters), normalization, soft thresholding, discretization, encoding the signal as a word distribution, and/or one or more other pre-processing functions. In some embodiments, the event prediction module may be configured to perform the one or more pre-processing steps to enhance the R-peaks of the ECG signal. FIG. 4B illustrates an example of a biomedical signal at different stages of filtering and encoding, in accordance with various embodiments. In an exemplary embodiment, the original noisy signal ("f(t)") is represented by the original noisy signal (Signal 1) depicted in FIG. 4B.

Referring back to FIG. 4A, the event prediction module may be configured to compute the moving average of the original signal and subtract the moving average from the original signal. For example, event prediction module may be configured to compute:

$$f_{av}(t) := \frac{1}{0.3} \int_{t-.15}^{t+.15} f(s)ds,$$

wherein $f_{av}(t)$ is the average value of f(s) on the interval [t−0.15, t+0.15]. This value is used in the baseline removal step of signal pre-processing. Baseline removal comprises replacing "f(t)" with "f(t)−$f_{av}$(t)", which removes baseline drift and waves of low frequency, capturing the high frequency peaks of greater significance. In an exemplary embodiment, the signal after the baseline removal step is represented by Signal 2 depicted in FIG. 4B.

Referring back to FIG. 4A, the event prediction module is configured to apply one or more morphological filters to the signal. For example, event prediction module may comprise applying a non-linear filter to the signal and/or one or more other morphological filters. A non-linear filter may remove non-important noise and other variations from the signal. For example, applying a non-linear filter to the signal may comprise peak filtering the signal. An example of a non-linear morphological filter that can be used to detect/predict AFib is given by the following formula:

$$f_{peak}(t) = \max\{0, f(t) - \max\{f(t-0.05), f(t+0.05)\}\}.$$

The function "$f_{peak}(t)$" is nonnegative and it is positive if and only if "f(t)>f(t−0.05)" and "f(t)>f(t+0.05)". In other words, the function "$f_{peak}(t)$" filters out narrow peaks of width 0.1. In an exemplary embodiment in which the biomedical signal comprises an ECG signal, this filter is sensitive to R-waves, but less sensitive to T-waves and P-waves. In analyzing ECG signals for AFib, narrow R-peaks are more significant than T-waves. Thus, applying a non-linear filter will enhance the R-peaks, suppress the other peaks or waves (e.g., T-waves and P-waves) and remove negative peaks. Peak filtering comprises replacing "f(t)" with "$f_{peak}(t)$". In an exemplary embodiment, the signal after the peak filter ("$f_{peak}(t)$") is represented by Signal 3 depicted in FIG. 4B. Note that the signal after the peak filter is applied is non-negative.

Referring back to FIG. 4A, the event prediction module may be configured to sample the biomedical signal down to a discrete signal. For example, the event prediction module may be configured to sample the biomedical signal down to a discrete signal "$x_1, x_2, \ldots, x_n$" of 20 Hz, where "$n = \lfloor t_0/20 \rfloor$" and $$x_k = \max\{f(t) | 0.05 \cdot (k-1) \leq t \leq 0.05 \cdot k\}.$$

The discrete signal "$x_k$" is represents the signal after discretization. In an exemplary embodiment, the signal after discretization ("$x_k$") is represented by Signal 4 depicted in FIG. 4B.

In various embodiments, the event prediction module may be configured to normalize the signal. In an exemplary embodiment, event prediction module may be configured to normalize the signal by dividing by the maximum over a 2 s interval. Event prediction module may be configured to replace "$x_k$" by "$x_k/\max\{x_{k-20}, x_{k-19}, \ldots, x_{k+20}\}$". After this step, "0≤$x_k$≤1" for all "k". The resulting signal will have positive peaks and a maximum absolute magnitude equal to 1—thus the signal is normalized to a scale 0 to 1. In an exemplary embodiment in which the biomedical signal comprises an ECG signal, if "$x_k$" is close to 1, it likely represents an R-peak or a similar feature contained within the original ECG signal. If "$x_k$" is close to 0, it likely does not represent a peak. In an exemplary embodiment, the normalized signal is represented by Signal 5 depicted in FIG. 4B.

In some embodiments, event prediction module may be configured to renormalize a signal. For example, a sequence may be renormalized according to a local relative magnitude.

In various embodiments, the event prediction module may be configured to apply a soft thresholding function to the signal. For example, event prediction module may be configured to apply a soft thresholding function to the normalized signal. In an exemplary embodiment, event prediction module may be configured to apply a soft thresholding function to the signal by replacing "$x_k$" with "$\phi(x_k)$" where "$\phi: [0,1] \to [0,1]$" is the function:

$$\phi(x) = \begin{cases} 1 & \text{if } x \geq .8 \\ 5x - 3 & \text{if } .6 \leq x \leq .8 \\ 0 & \text{if } x < .6. \end{cases}$$

In an exemplary embodiment, the signal after a soft thresholding function is applied may be represented by Signal 6 depicted in FIG. 4B.

Referring back to FIG. 4A (and as previously described), a pre-processed biomedical signal (e.g., an ECG signal) may be encoded into a word distribution "Q". In some embodiments, the pre-processed biomedical signal may be converted to an uncertain binary string before being encoded into a word distribution "Q". In various embodiments, the techniques described herein to pre-process a biomedical signal (including baseline removal, peak filtering, discretization, normalization, soft thresholding, and/or other pre-processing functions) may be performed by pre-processing component 906 of event prediction module 900 depicted in FIG. 9.

Figure 5:
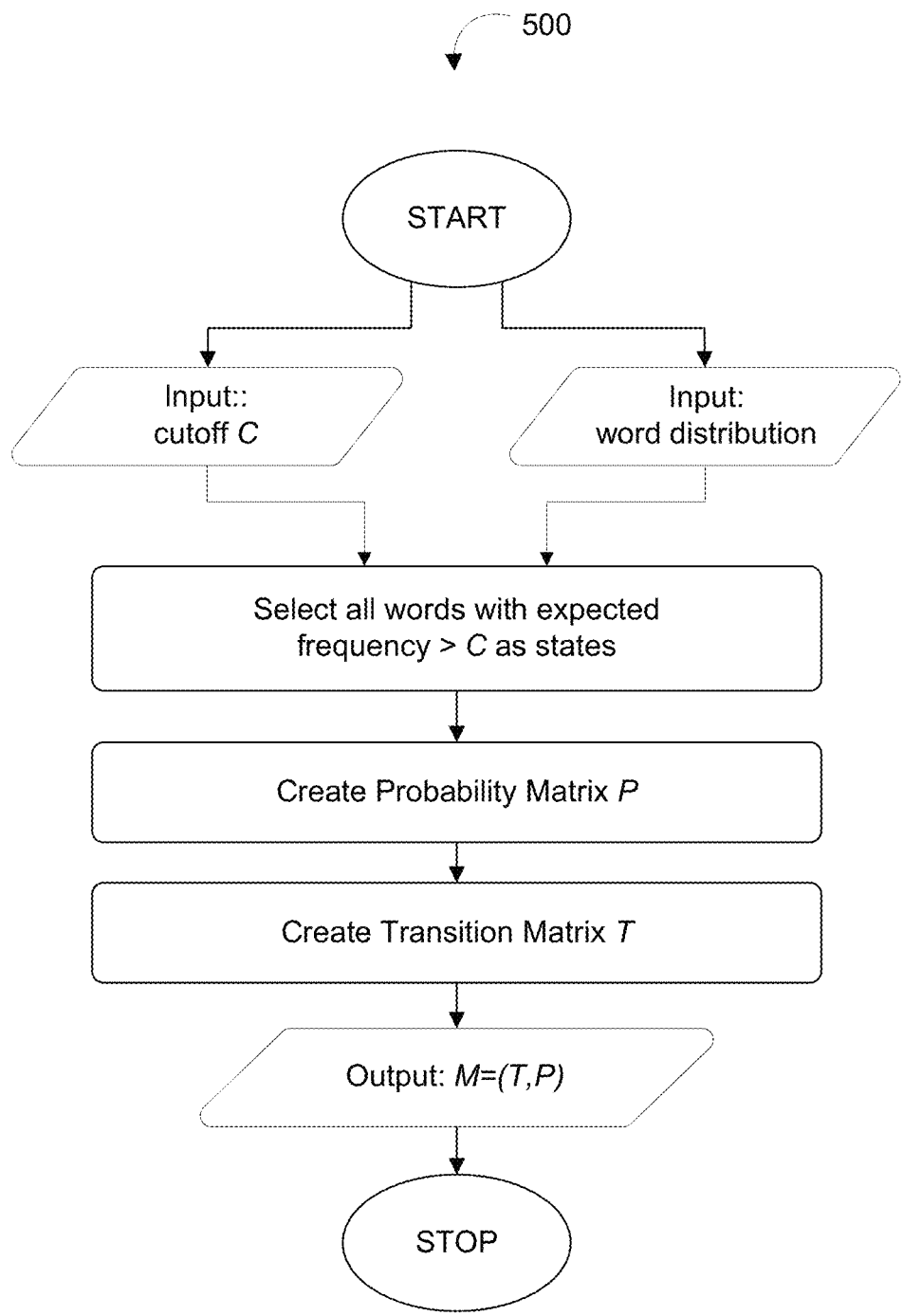
FIG. 5 contains an operational flow diagram illustrating an example workflow for creating a Markov chain algorithm, in accordance with various embodiments.

In various embodiments, event prediction module may be configured to create a Markov chain algorithm. Referring to FIG. 5, an operational flow diagram is depicted illustrating an example workflow 500 for creating a Markov chain algorithm, in accordance with various embodiments. In various embodiments, a parameter "C" and the word distribution "Q" may be input. Each of the words with expected an expected frequency greater than "C" are selected as states. Based on the words selected as states and the computed conditional probability vectors, a probability matrix "P" and a transition matrix "T" are created. The Markov Model "M=(P,T)" is the resulting output. In various embodiments, the features described herein to classify conditions based on one or more biomedical signals may be performed by Markov chain component 908 of event prediction module 900 depicted in FIG. 9.

Figure 6A:
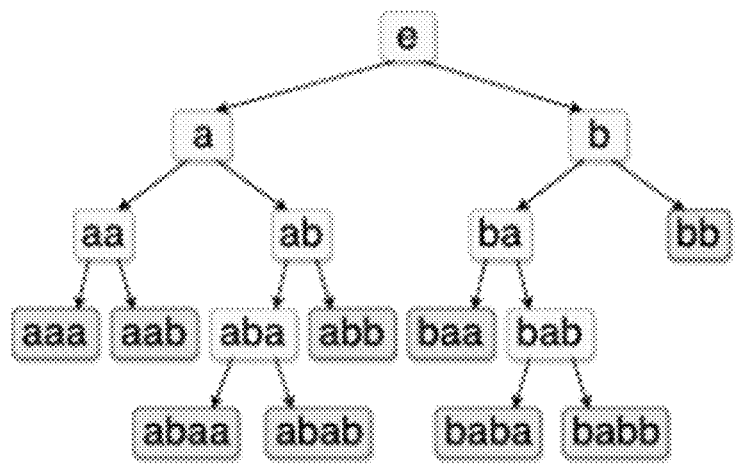
FIG. 6A illustrates an example of a relational map between words that is searched to create a Markov chain algorithm, in accordance with various embodiments.
Figure 6B:
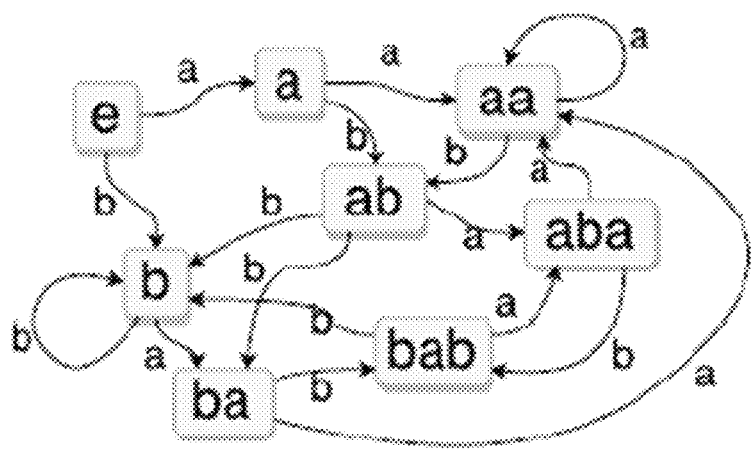
FIG. 6B illustrates an example of a Markov chain algorithm created based on the relational map between words depicted in FIG. 6A, in accordance with various embodiments.
Figure 7:
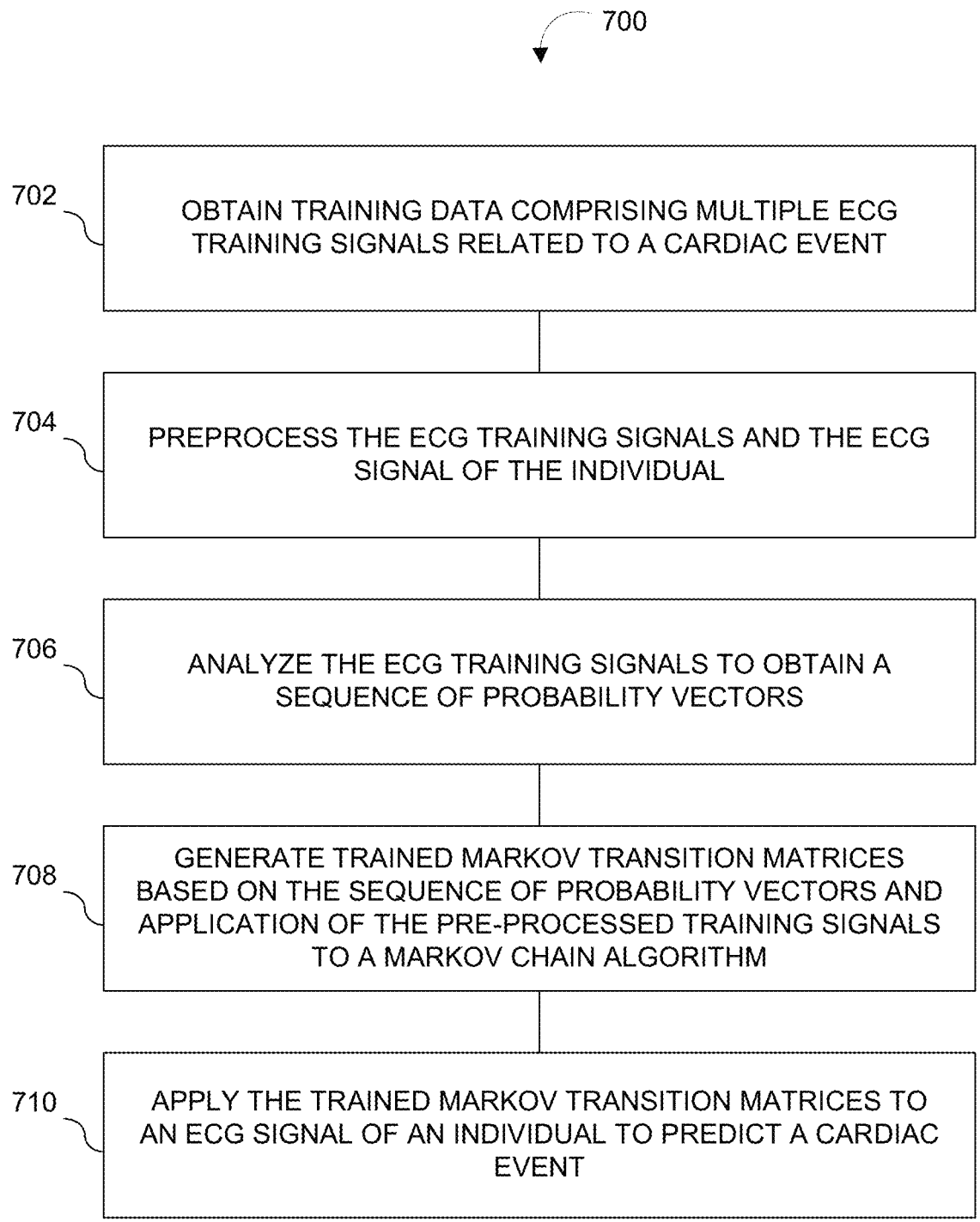
FIG. 7 is an example of a method for predicting and/or detecting cardiac events, in accordance with various embodiments.

For a word "u" and a random word "w", "y(u)" may be the expected number of times that "u" appears as a sub-word of "w". The states of the Markov model are the words "u" for which "y(u)≥C". The states are identified by depth-first search in the tree of all words. For example, FIG. 6 illustrates an example of a relational map between words (i.e., a "tree of words") that is searched to create a Markov chain algorithm, in accordance with various embodiments. In FIG. 6, the more lightly depicted words (e.g., e, a, b, aa, ab, ba, aba, and bab) appear at least "C" times and are the states, and the grayed out words (e.g., ba, aaa, aab, abb, baa, abaa, abab, baba, and babb) appear <"C" times. In this example there will be 8 states. FIG. 7 illustrates the Markov model obtained from the relational map between words illustrated in FIG. 6. The transition "T(a, aba)" is the largest suffix of "abaa" that is a state. Since "abaa" and "aba" are not states, we get "T(a, aba)=aa".

The function "P" is defined by:

$$P(u, a_i) = \frac{\gamma(ua_i)}{\gamma(u)}.$$

This number is a conditional property, that, after "u" is read as a sub-word of "w" that the next letter is "$a_i$". The number "$1-\Sigma_{i=1}^{d} P(u, a_i)$" is the probability that there is no next letter (i.e., the probability that a randomly chosen appearance of "u" as a sub-word "w" the suffix of "w". The largest suffix of $ua_i$ that is still a state in "S" is defined as "$T(u, a_i)$".

In various embodiments, the event prediction module may be configured to obtain a signal from an individual in real-time. In some implementations, the signal may be obtained from one or more sensors in an in-vehicle environment. For example, the signal may be obtained from one or more sensors incorporated into a vehicle (e.g., vehicle 10) that are configured to monitor a biomedical signal of a driver and/or passenger(s) of the vehicle. In some implementations, the signal may be obtained from a portable device. For example, the signal may be obtained from a wearable device affixed to the individual for which the biomedical signal relates. In some embodiments, the signal may be obtained from medical equipment designed to obtain the signal inside or outside of the hospital environment.

In various embodiments, the event prediction module may be configured to apply the trained Markov transition matrices to the signal obtained from an individual in real-time to automatically predict an upcoming cardiac event for the individual. In some embodiments, the obtained signal may be encoded as described in example workflow 300 for classifying conditions based on one or more biomedical signals, in accordance with various embodiments. The signal obtained in real-time from an individual may be encoded into a word distribution "Q", as described further herein. In various embodiments, the event prediction module may be configured to compute conditional probability vectors for the signal. For example, event prediction module may be configured to compute conditional probabilities that the obtained ECG signal represents one of the pre-cardiac event states "$CE_1, \ldots, CE_r$" or a normal state "n". For example, event prediction module may be configured to compute:

$$P(Q|M_{CE_i}) = E(P(u|M_{CE_i})) = \Sigma P(w=u|M_{CE_i})P(u),$$

wherein "$P(Q|M_{CE_i})$" is the expected probability that the Markov model "$M_{CE_i}$" produced the random word "w" (with probability distribution "Q"). Similarly, event prediction module may be configured to compute the expected probability "$P(Q|M_n)$" that the Markov model "$M_n$" produced the random word "w" with distribution "Q". If "$P(Q|M_{CE_i})$" is greatest among "$P(Q|M_n), P(Q|M_{CE_1}), \ldots, P(Q|M_{CE_r})$", the ECG is classified as "pre-cardiac event $CE_i$". If "$P(Q|M_n)$" is greatest among "$P(Q|M_n), P(Q|M_{CE_1}), \ldots, P(Q|M_{CE_r})$" the ECG is classified as "Normal". In various embodiments, the features described herein to classify conditions on signals obtained from individuals in real-time based on one or more biomedical signals may be performed by results component 910 of event prediction module 900 depicted in FIG. 9.

Various features described herein are described as being performed by one or more hardware processors configured by machine-readable, computer program instructions. Executing the instructions may cause the one or more processors to predict and/or detect medical conditions (e.g., a cardiac event) in real-time based on obtained biomedical signals. In some embodiments, some or all of the features described herein may be performed by a controller of a computing system. In some embodiments, some or all of the features described herein may be performed by one or more other processors that are configured to execute the features described herein by machine-readable instructions.

FIG. 7 is an example of a method 700 for predicting and/or detecting cardiac events, in accordance with various embodiments. The operations of method 700 presented below are intended to be illustrative and, as such, should not be viewed as limiting. In some implementations, method 700 may be accomplished with one or more additional operations not described, and/or without one or more of the operations discussed. In some implementations, two or more of the operations may occur substantially simultaneously. The described operations may be accomplished using some or all of the system components described in detail above.

In some embodiments, method 700 may be implemented in one or more processing devices (e.g., a digital processor, an analog processor, a digital circuit designed to process information, a central processing unit, a graphics processing unit, a controller, a microcontroller, an analog circuit designed to process information, a state machine, and/or other mechanisms for electronically processing information). The one or more processing devices may include one or more devices executing some or all of the operations of method 700 in response to instructions stored electronically on one or more electronic storage mediums. The one or more processing devices may include one or more devices configured through hardware, firmware, and/or software to be specifically designed for execution of one or more of the operations of method 700.

In an operation 702, method 700 may include obtaining training data comprising multiple biomedical signals related to a particular medical condition. In various embodiments, the biomedical signals may comprise ECG signals. In some embodiments, training data may be obtained from a database associated with a particular biomedical signal. In an exemplary embodiment in which the biomedical signal comprises an ECG signal, the training data may be obtained from the Physionet/CinC 2017 database, and/or one or more other databases that store ECG signals. In some embodiments, signals obtained from individuals in real-time may be stored and later used to train a machine learning algorithm to predict and/or detect one or more medical conditions. In some implementations, operation 702 may be performed by a processor component the same as or similar to training component 902 (shown in FIG. 9 and described herein).

In an operation 704, method 700 may include preprocessing the training signals and signals obtained for an individual in real-time. In various embodiments, the signals obtained may comprise ECG signals. In various embodiments, pre-processing the training signals and the signals obtained for an individual in real-time may comprise baseline removal, peak filtering, discretization, normalization, soft thresholding, and/or other pre-processing functions. In some embodiments, pre-processing the signals may comprise removing baseline drift and waves of low frequency by subtracting the moving average from each signal. In some embodiments, pre-processing signals the may comprise applying a non-linear filter to remove variations in each signal, wherein variations in the signal include noise. In some embodiments, pre-processing the signals may comprise sampling each signal to a discrete signal. In some embodiments, pre-processing the signals may comprise normalizing each signal between a first value and a second value (e.g., 0 and 1). In some embodiments, pre-processing the signals may comprise applying the soft thresholding function to the signal. In some embodiments, pre-processing the signals may comprise renormalizing the signal according to a local relative magnitude. In some embodiments, pre-processing the training signals may comprise extracting from each signal a pre-event signal that spans a predetermined time interval before the cardiac event, wherein the pre-event training signals are applied to the Markov chain algorithm to train a machine learning algorithm. In some embodiments, pre-processing the signals may comprise identifying patterns within the signal and assigning identifiers to each pattern identified. In some implementations, operation 704 may be performed by a processor component the same as or similar to pre-processing component 906 (shown in FIG. 9 and described herein).

In an operation 706, method 700 may include analyzing the training signals to obtain a sequence of probability vectors. For example, based on the Markov model "$M_{CE_i}$" for the Pre-Cardiac Event cases $CE_1, \ldots, CE_r$ and the Markov model "$M_n$" for the Normal case obtained during the training phase, conditional probabilities may be computed indicating whether a signal comprising certain patterns represents one of the "Pre-Cardiac Event" states or a "Normal" state. In some implementations, operation 706 may be performed by a processor component the same as or similar to classification component 904 or Markov chain component 908 (shown in FIG. 9 and described herein).

In an operation 708, method 700 may include generating trained Markov transition matrices based on the sequence of probability vectors and application of the pre-processed training signals to a Markov chain algorithm. In various embodiments, training signals may be applied to a Markov chain prediction algorithm to train a machine learning algorithm using the sequence of probability vectors obtained by analyzing the ECG training signals, resulting in trained Markov transition matrices. In some implementations, operation 708 may be performed by a processor component the same as or similar to Markov chain component 908 (shown in FIG. 9 and described herein).

In an operation 710, method 700 may include applying the trained Markov transition matrices to a biomedical signal of an individual to predict the occurrence of a particular cardiac event. In various embodiments, an alert may be generated and communicated when a cardiac event has been predicted or detected. In some implementations, operation 708 may be performed by a processor component the same as or similar to Markov chain component 908 (shown in FIG. 9 and described herein).

Figure 8:
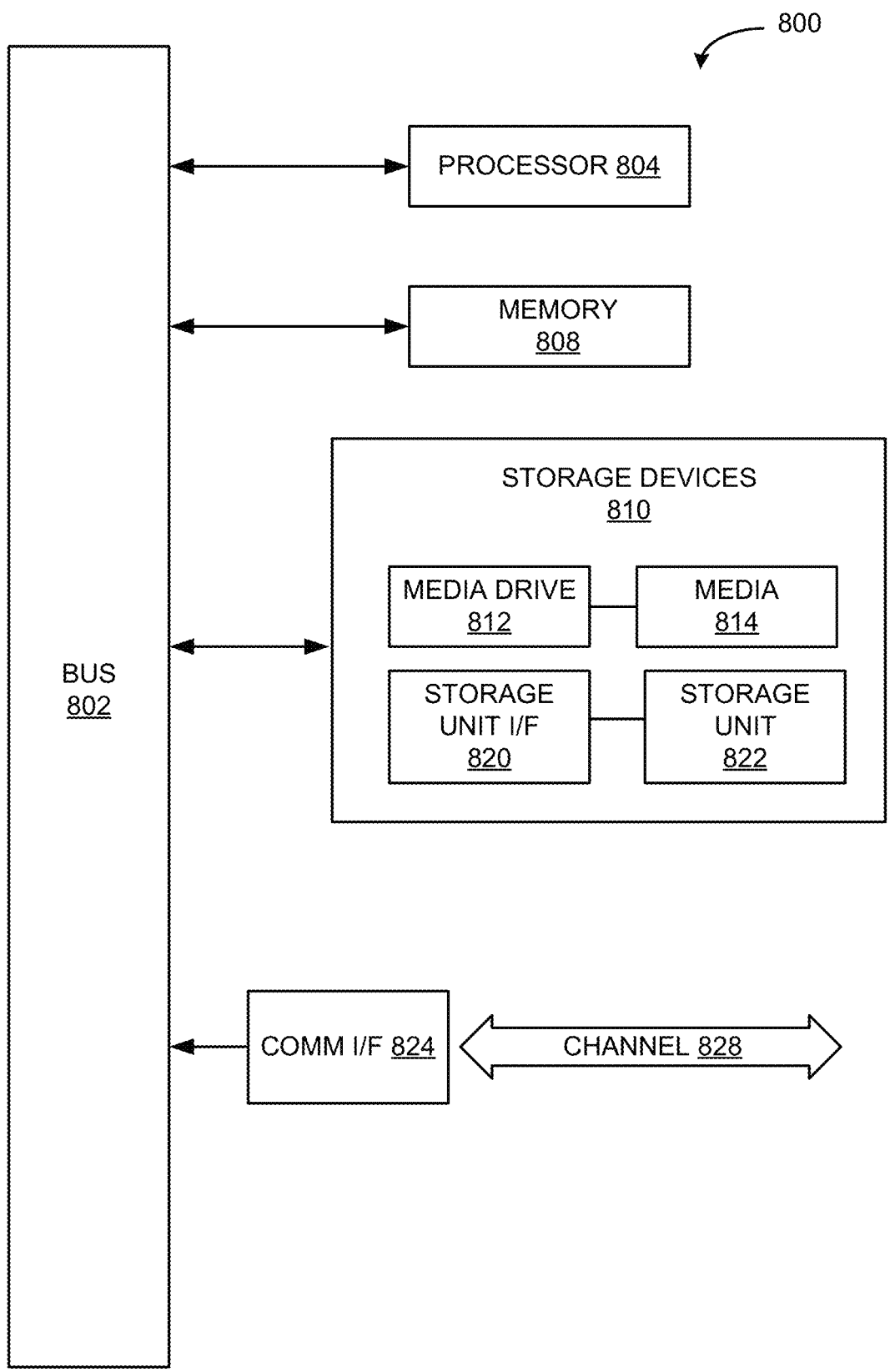
FIG. 8 illustrates an example computing module that may be used in implementing various features of embodiments of the disclosed technology.

As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete circuits or the functions and features described can be shared in part or in total among one or more circuits. In other words, as would be apparent to one of ordinary skill in the art after reading this description, the various features and functionality described herein may be implemented in any given application and can be implemented in one or more separate or shared circuits in various combinations and permutations. Even though various features or elements of functionality may be individually described or claimed as separate circuits, one of ordinary skill in the art will understand that these features and functionality can be shared among one or more common circuits, and such description shall not require or imply that separate circuits are required to implement such features or functionality.

Where modules are implemented in whole or in part using software, in one embodiment, these software elements can be implemented to operate with a computing or processing system capable of carrying out the functionality described with respect thereto. One such example computing system is shown in FIG. 8. Various embodiments are described in terms of this example-computing system 800. After reading this description, it will become apparent to a person skilled in the relevant art how to implement the technology using other computing systems or architectures.

Referring now to FIG. 8, computing system 800 may represent computing or processing capabilities within a large-scale system comprising a plurality of hardware components of various types that may communicate within and across partitions. Computing system 800 may also represent, for example, computing or processing capabilities found within mainframes, supercomputers, workstations or servers; or any other type or group of special-purpose or general-purpose computing devices as may be desirable or appropriate for a given application or environment. Computing system 800 might also represent computing capabilities embedded within or otherwise available to a given device.

Computing system 800 might include, for example, one or more processors, controllers, control modules, or other processing devices, such as a processor 804. Processor 804 might be implemented using a general-purpose or special-purpose processing engine such as, for example, a microprocessor (whether single-, dual- or multi-core processor), signal processor, graphics processor (e.g., GPU) controller, or other control logic. In the illustrated example, processor 804 is connected to a bus 802, although any communication medium can be used to facilitate interaction with other components of computing system 800 or to communicate externally.

Computing system 800 might also include one or more memory modules, simply referred to herein as main memory 808. For example, in some embodiments random access memory (RAM) or other dynamic memory, might be used for storing information and instructions to be executed by processor 804. Main memory 808 might also be used for storing temporary variables or other intermediate information during execution of instructions to be executed by processor 804. Computing system 800 might likewise include a read only memory ("ROM") or other static storage device coupled to bus 802 for storing static information and instructions for processor 804.

The computing system 800 might also include one or more various forms of information storage mechanism 810, which might include, for example, a media drive 812 and a storage unit interface 820. The media drive 812 might include a drive or other mechanism to support fixed or removable storage media 814. For example, a hard disk drive, a floppy disk drive, a magnetic tape drive, an optical disk drive, a CD or DVD drive (R or RW), a flash drive, or other removable or fixed media drive might be provided. Accordingly, storage media 814 might include, for example, a hard disk, a floppy disk, magnetic tape, cartridge, optical disk, a CD or DVD, or other fixed or removable medium that is read by, written to or accessed by media drive 812. As these examples illustrate, the storage media 814 can include a computer usable storage medium having stored therein computer software or data.

In alternative embodiments, information storage mechanism 810 might include other similar instrumentalities for allowing computer programs or other instructions or data to be loaded into computing system 800. Such instrumentalities might include, for example, a fixed or removable storage unit 822 and an interface 820. Examples of such storage units 822 and interfaces 820 can include a program cartridge and cartridge interface, a removable memory (for example, a flash memory or other removable memory module) and memory slot, a flash drive and associated slot (for example, a USB drive), a PCMCIA slot and card, and other fixed or removable storage units 822 and interfaces 820 that allow software and data to be transferred from the storage unit 822 to computing system 800.

Computing system 800 might also include a communications interface 824. Communications interface 824 might be used to allow software and data to be transferred between computing system 800 and external devices. Examples of communications interface 824 might include a modem or softmodem, a network interface (such as an Ethernet, network interface card, WiMedia, IEEE 802.XX, Bluetooth® or other interface), a communications port (such as for example, a USB port, IR port, RS232 port, or other port), or other communications interface. Software and data transferred via communications interface 824 might typically be carried on signals, which can be electronic, electromagnetic (which includes optical) or other signals capable of being exchanged by a given communications interface 824. These signals might be provided to communications interface 824 via a channel 828. This channel 828 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 808, storage unit 820, media 814, and channel 828. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing system 800 to perform features or functions of the disclosed technology as discussed herein.

Referring now to FIG. 9, event prediction module 900 may be configured to predict and/or detect medical conditions based on one or more obtained biomedical signals, in accordance with various embodiments and features described herein. The various components of event prediction module 900 depict various sets of functions that may be implemented by computer program instructions of event prediction module 900. Event prediction module 900 may be configured to program electronic control unit 50 and/or computer system 800 to predict and/or detect medical conditions based on one or more obtained biomedical signals using all or a portion of the components of event prediction module 900 illustrated in FIG. 9.

Event prediction module 900 may include a training component 902, a classification component 904, a pre-processing component 906, a Markov chain component 908, a results component 910, and/or other components. One or more of training component 902, classification component 904, pre-processing component 906, Markov chain component 908, and results component 910 may be coupled to one another or to components not shown in FIG. 9. Each of the components of event prediction module 900 may comprise various instructions that program a computer system (e.g., electronic control unit 50 and/or computer system 800) to perform various operations, each of which are described in greater detail herein. As used herein, for convenience, the various instructions will be described as performing an operation, when, in fact, the various instructions program the processors (and therefore computer system) to perform the operation.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system for predicting a cardiac event, the system comprising:
    one or more sensors configured to monitor a biomedical signal of an individual in real-time;
    one or more physical processors programmed with computer program instructions that, when executed by the one or more physical processors, configure the system to:
        receive a trained machine learning (ML) model that relates a first plurality of biomedical training signals to the cardiac event and a second plurality of biomedical training signals when the cardiac event does not occur;
        receive the biomedical signal of the individual, wherein the biomedical signal is received by the one or more sensors, and wherein the individual is a driver or a passenger of a vehicle;
        filter the biomedical signal to a discrete signal $x_k$ where: $x_k = \max\{f(t) | 0.05 \cdot (k-1) \leq t \leq 0.05 \cdot k\}$, where $f(t)$ is the biomedical signal, t is time, and k is an integer value; and
        determine a conditional probability of the cardiac event by applying the discrete signal of the individual to the trained ML model.

2. The system of claim 1, further comprising:
    when the conditional probability associated with the cardiac event is the greatest among conditional probabilities of the trained ML model, perform an action identifying the individual will likely experience the cardiac event.

3. The system of claim 1, wherein the trained machine learning (ML) model is a Markov model.

4. The system of claim 1, wherein the one or more physical processors are communicatively coupled to an electronic control unit of the vehicle.

5. The system of claim 1, wherein the one or more sensors are affixed to the individual while the individual is the driver or the passenger of the vehicle.

6. The system of claim 1, wherein the ML model is trained using the first plurality of biomedical training signals related to the cardiac event, and the second plurality of biomedical training signals when the cardiac event does not occur.

7. The system of claim 1, wherein the one or more sensors configured to monitor the biomedical signal is incorporated with a steering wheel of the vehicle, and wherein the biomedical signal of the individual is received through the steering wheel.

8. A method for predicting a cardiac event, the method being implemented in a computer system having: one or more sensors configured to monitor a biomedical signal of an individual in real-time; and one or more physical processors programmed with computer program instructions that, when executed by the one or more physical processors, cause the computer system to perform the method, the method comprising:
 receiving a trained machine learning (ML) model that relates a first plurality of biomedical training signals to the cardiac event and a second plurality of biomedical training signals when the cardiac event does not occur;
 receiving the biomedical signal of the individual, wherein the biomedical signal is received by the one or more sensors, and wherein the individual is a driver or a passenger of a vehicle;
 filter the biomedical signal to a discrete signal $x_k$ where: $x_k = \max\{f(t) | 0.05 \cdot (k-1) \leq t \leq 0.05 \cdot k\}$, where $f(t)$ is the biomedical signal, t is time, and k is an integer value; and
 determining a conditional probability of the cardiac event by applying the discrete signal of the individual to the trained ML model.

9. The method of claim 8, further comprising:
 when the conditional probability associated with the cardiac event is the greatest among conditional probabilities of the trained ML model, performing an action identifying the individual will likely experience the cardiac event.

10. The method of claim 8, wherein the trained machine learning (ML) model is a Markov model.

11. The method of claim 8, wherein the one or more physical processors are communicatively coupled to an electronic control unit of the vehicle.

12. The method of claim 8, wherein the one or more sensors are affixed to the individual while the individual is the driver or the passenger of the vehicle.

13. The method of claim 8, wherein the ML model is trained using the first plurality of biomedical training signals related to the cardiac event, and the second plurality of biomedical training signals when the cardiac event does not occur.

14. A non-transitory computer readable media including instructions that, when executed by one or more processors, cause the one or more processors to:
 receive a trained machine learning (ML) model that relates a first plurality of biomedical training signals to a cardiac event and a second plurality of biomedical training signals when the cardiac event does not occur;
 receive a biomedical signal of a individual, wherein the biomedical signal is received by one or more sensors, and wherein the individual is a driver or a passenger of a vehicle;
 filter the biomedical signal to a discrete signal $x_k$ where: $x_k = \max\{f(t) | 0.05 \cdot (k-1) \leq t \leq 0.05 \cdot k\}$, where $f(t)$ is the biomedical signal, t is time, and k is an integer value; and
 determine a conditional probability of the cardiac event by applying the discrete signal of the individual to the trained ML model.

15. The non-transitory computer readable media of claim 14, further configured to:
 when the conditional probability associated with the cardiac event is the greatest among conditional probabilities of the trained ML model, perform an action identifying the individual will likely experience the cardiac event.

16. The non-transitory computer readable media of claim 14, wherein the trained machine learning (ML) model is a Markov model.

17. The non-transitory computer readable media of claim 14, wherein the computer readable media are communicatively coupled to an electronic control unit of the vehicle.

18. The non-transitory computer readable media of claim 14, wherein the computer readable media is communicatively coupled with sensors, and wherein the sensors are affixed to the individual while the individual is the driver or the passenger of the vehicle.

19. The non-transitory computer readable media of claim 14, wherein the ML model is trained using the first plurality of biomedical training signals related to the cardiac event, and the second plurality of biomedical training signals when the cardiac event does not occur.

* * * * *